United States Patent [19]
Hofmann et al.

[11] Patent Number: 5,900,221
[45] Date of Patent: * May 4, 1999

[54] PROCESS OF PREPARING A SOLUTION OF CESIUM AND RUBIDIUM SALTS

[75] Inventors: Hartmut Hofmann, Bad Soden; Klaus Köbele, Dietzenbach; Horst Prinz, Friedberg; Klaus Schade, Wiesbaden, all of Germany

[73] Assignee: Metallgesellschaft Aktiengesellschaft, Frankfurt, Germany

[ * ] Notice: This patent is subject to a terminal disclaimer.

[21] Appl. No.: 08/649,712

[22] PCT Filed: Nov. 2, 1994

[86] PCT No.: PCT/EP94/03651

§ 371 Date: Sep. 18, 1996

§ 102(e) Date: Sep. 18, 1996

[87] PCT Pub. No.: WO95/13986

PCT Pub. Date: May 26, 1995

[30] Foreign Application Priority Data

Nov. 16, 1993 [DE] Germany .............................. 43 39 062

[51] Int. Cl.$^6$ .............................. C01D 3/00; C01D 17/00; C22B 26/00
[52] U.S. Cl. .......................... 423/189; 423/203; 423/165; 423/179
[58] Field of Search ..................................... 423/189, 203, 423/165, 179

[56] References Cited

U.S. PATENT DOCUMENTS 3,207,571 9/1965 Berthold .
3,489,509 1/1970 Johnson .
5,593,650 1/1997 Prinz et al. .............................. 423/203

FOREIGN PATENT DOCUMENTS

94/11303 5/1994 WIPO .

OTHER PUBLICATIONS

Chem. Abstract: 100: 160074p, 1984, no month.
Chem. Abstract: 79: 4949v, 1973, no month.
Chem. Abstract: 73: 79009y, 1970, no month.
Tsnetnye Metallurgy, The Soviet J. Non–Ferrous Met., Bd. 2, Nr. 5, 1961, no month, pp. 57–59.

*Primary Examiner*—Steven Bos
*Attorney, Agent, or Firm*—Michael J. Striker

[57] ABSTRACT

The process for preparing a cesium and rubidium salt-containing solution includes a hydrothermal digestion of an uncalcined pollucite and/or calcined lepidolite particulate having an average particle size up to 0.5 mm with an aqueous solution of $Ca(OH)_2$ in a suspension with a mole ratio of $SiO_2$ to CaO of from 1:2.5 to 1:1.25 in a rotary tubular autoclave at a digestion temperature of 200 to 280° C., under a pressure of from 15 to 65 bar and at a suspension density between 8 and 18% by weight for from 0.5 to 3 hours; filtering the suspension to remove insoluble solids and to form a digestion filtrate; adding at least one acid or acid anhydride to the digestion filtrate to adjust its pH to 6 and to form the cesium and rubidium salt-containing solution; and performing an evaporation after the hydrothermal digestion to obtain an increase in concentration of cesium salts and rubidium salts in the cesium and rubidium salt-containing solution and to adjust a density of the cesium and rubidium salt-containing solution to from 1.6 to 3.3 g/cm$^3$. An optional aeration of the digestion filtrate with carbon dioxide to remove lithium and calcium ions in precipitated carbonates may be performed.

5 Claims, No Drawings

PROCESS OF PREPARING A SOLUTION OF CESIUM AND RUBIDIUM SALTS

BACKGROUND OF THE INVENTION

This invention relates to a process of preparing a solution which contains cesium and rubidium salts and has a density between 1.6 and 3.3 g/cm$^3$. This process includes hydrothermal digestion of uncalcined pollucite and/or calcined lepidolite with an aqueous solution of Ca(OH)$_2$ at a digestion temperature of 200 to 280° C. and under a pressure from 15 to 65 bars and at a suspension density between 8 and 18% by weight for 0.5 to 3 hours, separation from the insoluble solids, optional removal of calcium ions and lithium ions by an aeration with carbon dioxide and removal of the precipitated carbonates from the digestion filtrate and formation of the salts of cesium and rubidium by an addition of an acid or an acid anhydride to adjust the pH to at least 6. The density of the solution of cesium and rubidium salts is increased by an evaporation performed after the digestion, after the removal of the precipitated carbonates and/or after the addition of the acid or the acid anhydride.

The periodical "Tsvetnye metally—The Soviet Journal of Non-Ferrous Metals", Volume II, No. 5, pages 57 to 59 (1961) discloses a method of preparing cesium carbonate by a hydrothermal digestion of a pollucite-spodumene concentrate. The calcined minerals are subjected to a hydrothermal digestion with an aqueous solution of Ca(OH)$_2$ at 220° C. and under a pressure of 20 atm for four hours. Optimum digestion conditions are achieved with 3 moles Ca(OH)$_2$ per mole SiO$_2$. 88.3 percent by weight of the cesium contained in the mineral can be recovered and the alumo-cesium-alum can be recrystallized to prepare a cesium salt having a purity >99%. The Chemical Abstracts Reference 79/4949v (1973) discloses the conversion of Cs$_2$CO$_3$ to CsHCO$_2$ in a process in which the carbonate is reacted with formic acid in water.

Besides, the unpublished German Patent Application P 42 37 954.7 describes a process of preparing solutions which contain cesium salts and rubidium salts and have a density from 1.6 to 3.3 g/cm$^3$ by a hydrothermal digestion of minerals which contain cesium and rubidium. That process has the process features mentioned first hereinbefore.

SUMMARY OF THE INVENTION

It is an object of the invention to provide a process for preparing a solution of cesium and rubidium salts of the above-described type, which has a high yield in comparison to prior art processes and a suspension density above 8% by weight, permits a decrease of the fineness to which the starting materials must be ground and utilizes calcium oxide in a slight excess over silica.

That object is accomplished in accordance with the invention in a method of the above-described type in which uncalcined pollucite and/or calcined lepidolite having an average particle size up to 0.5 mm is digested in a rotary tubular autoclave and the mole ratio of SiO$_2$ to CaO is in the range between 1:2.5 and 1:1.25.

The suspension density is defined by the concentration of the pollucite and/or lepidolite and of the undissolved CaO and/or Ca(OH)$_2$ in water.

It is surprising that it is possible under the stated process conditions to recover more than 90% by weight of the cesium and rubidium contained in the mineral by the hydrothermal digestion in a rotary tubular autoclave and to recover cesium and rubidium at low cost as a solution which contains cesium salts and rubidium salts and has a density between 1.6 and 3.3 g/cm$^3$. In that process the grinding expenditure is relatively low because the minerals are used with an average particle size up to 0.5 mm and the surplus of CaO over the SiO$_2$ contained in the mineral is also comparatively low.

In a preferred embodiment of the invention the first filtrate obtained after the separation of the carbonates and/or the post-filtration washing liquid is used as a mashing liquid for the next digestion. With that feature of the process in accordance with the invention it is possible to prepare solutions which contain cesium salts and rubidium salts and have a density from 1.6 to 3.3 g/cm$^3$ and to obtain digested solutions which need not be evaporated to a high concentration so that the process is more economical.

The solution of cesium salts and rubidium salts is advantageously prepared in a preferred embodiment of the method in which the digested solution obtained after separation of calcium ions and lithium ions is reacted with an acid or acids selected from the group consisting of formic acid, acetic acid, citric acid, hydrochloride acid, hydrobromic acid and sulfuric acid or an acid anhydride or acid anhydrides selected from the group consisting of carbon monoxide, molybdenum trioxide and tungsten trioxide.

The density of the solution of cesium salts and rubidium salts can desirably be varied within wide ranges when saturated solutions of an alkali salt or alkaline earth salt are admixed, whereas the anions of the two salt solutions are the same.

Preferably, the solutions of cesium formate and rubidium formate which have been prepared by the process are mixed with saturated potassium formate solutions to adjust its density to from 1.6 to 2.26 g/ml, and solutions of cesium bromide and rubidium bromide which have been prepared by the process are mixed with saturated calcium bromide solutions to provide salt solutions having densities between 1.68 and 1.80 g/ml.

It has been found that it is desirable for the entire process to use the separated carbonates for the production of lithium and to add the insoluble solids left after the hydrothermal digestion as a flux to ground raw materials for making cement. As a result, virtually no materials to be disposed of are produced by the proposed process.

The invention will be explained more in detail with reference to the following examples.

EXAMPLES

Analysis of Pollucite used in Examples

| Content of | Original pollucite % by weight |
|---|---|
| Cs | 23.5 |
| Pb | 0.97 |
| Al | 8.9 |
| Na | 1.07 |
| K | 1.09 |
| Li | 0.30 |
| Ca | 0.08 |
| SiO$_2$ | 51.6 |

The following experiments were carried out with the uncalcined pollucite.

Example 1

A suspension having a density of 12% by weight and comprising pollucite which has an average particle size of 0.01 mm, calcium hydroxide, and water is prepared and preheated in a slurrying vessel. The mole ratio of $SiO_2$ to CaO is 1:1.4. The suspension has a volume of 8 m³. That suspension is fed to a rotary tubular autoclave, which is mounted for rotation about a horizontal axis and has a total capacity of about 13 m³ and a working volume of about 9 m³. The rotary tubular autoclave can be rotated by a geared drive at two speeds (4 and 7 revolutions per minute). Heating is performed by a direct injection of steam into the suspension. The pollucite is digested during rotation at a temperature of about 220° C. and under a pressure of 21 to 23 bars for 1.5 hours. After the reaction time a pressure relief is effected and the residual pressure is used to force the suspension into the filtering vessel. The autoclave is flushed with water at about 150° C. and the washing liquid is also forced into the filtering vessel. The digested solution is separated from the insoluble solids in a drum filter. The filter cake is subsequently mashed with water and is fed to high-pressure filter tubes. Under pressures of up to 150 bars the resulting suspension is dewatered in the high pressure filter tubes. The resulting residual moisture content is below 30%. The clear solution consisting of the filtrate and washing liquid is evaporated. As the evaporation of water proceeds, dissolved solids are precipitated. After an evaporation to about 15% of the original volume, carbon dioxide is injected into the remaining suspension in order to precipitate calcium ions and lithium ions as carbonate. A clear filtrate is subsequently recovered over a suction filter. Formic acid is gradually added to the filtrate until a pH of 6 has been reached. The results stated in Table 1 were obtained by the treatment of a pollucite having an average particle size of 0.01 mm.

Example 2

The hydrothermal digestion is carried out as in Example 1 with the difference that the pollucite has an average particle size of 0.2 mm. The results of that digestion are stated in Table 2.

Example 3

The hydrothermal digestion is carried out as in Example 1 with the difference that the filtered liquid used to wash the insoluble solids is used in mashing for the following digestion. The results are stated in Table 3. In Table 3, the amount of cesium in each charge of freshly supplied mineral is stated in column 2 and the amounts of cesium in the post-filtration washing liquid from the preceding digestion are stated in column 3. The total amount of the first filtrate and the post-filtration washing liquid is stated in column 4. The amount of cesium in the digestion filtrate consisting of the first filtrate and the post-filtration washing liquid is stated in column 5 in percent by weight and in column 6 as the absolute amount. The yield of cesium in percent of its content in the mineral is stated in column 7.

Example 4

The hydrothermal digestion is carried out in analogy to Example 3 with the difference that the feed pollucite has an average particle size of 0.2 mm. The results are compiled in Table 4, in which the columns have the same meaning as in Table 3.

Example 5

Solutions which contain cesium salts and rubidium salts and have a density from 1.6 to 2.26 g/ml are prepared by mixing a solution of cesium formate and rubidium formate which has been prepared in accordance with the invention with a saturated solution of potassium formate as stated in Table 5.

Example 6

Solutions of cesium which contain cesium salts and rubidium salts and have density from 1.68 to 1.80 g/ml are prepared by mixing solutions of cesium bromide and rubidium bromide which have been prepared in accordance with the invention with saturated solutions of calcium bromide as stated in Table 6.

TABLE 1

Digestion of Pollucite with $Ca(OH)_2$
$SiO_2:CaO = 1:1.4$; suspension density 12%; 220° C.;
reaction time 1.5 hours; average particle size 0.01 mm

| Feed Pollucite | Yield Filtrate | | Yield based on feed pollucite | |
|---|---|---|---|---|
| Cs kg | kg | wt % | Cs kg | Cs wt. % |
| 102 | 14760 | 0.63 | 93.2 | 91.4 |

TABLE 2

Digestion of Pollucite with $Ca(OH)_2$
$SiO_2:CaO = 1:1.4$; suspension density 12%; 220° C.;
reaction time 1.5 hours; average particle size 0.2 mm

| Feed Pollucite | Yield Filtrate | | Yield based on feed pollucite | |
|---|---|---|---|---|
| Cs kg | kg | wt % | Cs kg | Cs wt. % |
| 89 | 13250 | 0.60 | 80.1 | 90 |

TABLE 3

Digestion of Pollucite With Recycling of
Post-filtration Washing Liquid
$SiO_2:CaO = 1:1.4$; suspension density 12%; 220° C.;
reaction time 1.5 hours; average particle size 0.01 mm

| | Feed | | Yield | | Yield based on feed | |
|---|---|---|---|---|---|---|
| Exp. | Pollucite | Solution | Filtrate | | pollucite | |
| No. | Cs kg | Cs kg | kg | wt. % | Cs kg | Cs wt. % |
| 2 | 102 | 6.7 | 14763 | 0.67 | 99.5 | 91 |
| 3 | 102 | 12.8 | 14753 | 0.74 | 108.7 | 94 |
| 4 | 102 | 18.9 | 14425 | 0.79 | 113.7 | 93 |
| 5 | 102 | 15.3 | 14666 | 0.72 | 106.1 | 89 |
| 6 | 102 | 17.0 | 14522 | 0.75 | 108.8 | 90 |

TABLE 4

Digestion of Pollucite With Recycling of
Post-filtration Washing Liquid
$SiO_2:CaO$ = 1:1.4; suspension density 12%; 220° C.;
reaction time 1.5 hours; average particle size 0.2 mm

| Exp. No. | Feed Pollucite Cs kg | Feed Solution Cs kg | Yield Filtrate kg | Yield Filtrate wt. % | Yield based on feed pollucite Cs kg | Yield based on feed pollucite Cs wt. % |
|---|---|---|---|---|---|---|
| A | 89 | 7.2 | 13291 | 0.66 | 87.3 | 90 |
| B | 89 | 10.6 | 13081 | 0.69 | 90.2 | 89.4 |
| C | 89 | 14.7 | 13100 | 0.70 | 92.9 | 89.8 |
| D | 89 | 16.0 | 13300 | 0.73 | 97.0 | 91 |
| E | 89 | 15.2 | 13424 | 0.71 | 95.8 | 90.6 |

TABLE 5

Mixing of a Solution of HCOOCs/Rb Prepared From Pollucite
With a Saturated Solution of HCOOK at 20° C.

| Volume percent HCOOCs/Rb:HCOOK | Weight percent HCOOCs/Rb:HCOOK | Density at 20° C. g/ml |
|---|---|---|
| 100:— | 100:— | 2.264 |
| 90:10 | 92.9:7.1 | 2.194 |
| 80:20 | 85.2:14.8 | 2.125 |
| 70:30 | 77.1:22.9 | 2.055 |
| 60:40 | 68.4:31.6 | 1.986 |
| 50:50 | 59.1:40.9 | 1.916 |
| 40:60 | 49.0:51.0 | 1.846 |
| 30:70 | 38.2:61.8 | 1.777 |
| 20:80 | 26.5:73.5 | 1.707 |
| 10:90 | 13.8:86.2 | 1.638 |
| —:100 | —:100 | 1.568 |

TABLE 6

Mixing of a Solution of Cs/RbBr With a Saturated Solution of $CaBr_2$

| Volume percent Cs/RbBr:CaBr$_2$ | Weight percent Cs/RbBr:CaBr$_2$ | Density at 20° C. g/ml |
|---|---|---|
| 100:— | 100:— | 1.682 |
| 90:10 | 89.3:10.7 | 1.695 |
| 80:20 | 78.8:21.2 | 1.708 |
| 70:30 | 68.4:31.6 | 1.721 |
| 60:40 | 58.2:41.8 | 1.734 |
| 50:50 | 48.1:51.9 | 1.747 |
| 40:60 | 38.2:61.8 | 1.760 |
| 30:70 | 28.5:71.5 | 1.773 |
| 20:80 | 18.8:81.2 | 1.786 |
| 10:90 | 9.3:90.7 | 1.799 |
| —:100 | —:100 | 1.812 |

We claim:

1. A process for preparing a cesium and rubidium salt-containing solution, said process comprising the steps of:
   a) performing a hydrothermal digestion of an uncalcined pollucite and/or calcined lepidolite particulate having an average particle size up to 0.5 mm with an aqueous solution of $Ca(OH)_2$ in a suspension with a mole ratio of $SiO_2$ to CaO of from 1:2.5 to 1:1.25 in a rotary tubular autoclave at a digestion temperature of 200 to 280° C., under a pressure of from 15 to 65 bars and at a suspension density between 8 and 18% by weight for from 0.5 to 3 hours;
   b) filtering said suspension to remove insoluble solids and to form a digestion filtrate;
   c) adding at least one acid or acid anhydride to said digestion filtrate to adjust a pH of said digestion filtrate to 6 and to form the cesium and rubidium salt-containing solution; and
   d) performing an evaporation after the performing of the hydrothermal digestion to obtain an increase in concentration of cesium salts and rubidium salts in the cesium and rubidium salt-containing solution and to adjust a density of the cesium and rubidium salt-containing solution to from 1.6 to 3.3 g/cm$^3$.

2. The process as defined in claim 1, further comprising injecting carbon dioxide into said digestion filtrate to remove lithium and calcium ions and filtering said digestion filtrate after the aerating to remove precipitated carbonates therefrom and to form another filtrate.

3. The process as defined in claim 2, further comprising using said another filtrate and/or a post-filtration wash liquid used to wash said carbonates as a mashing liquid for a subsequent digestion.

4. The process as defined in claim 1, wherein said suspension density is about 15% by weight and said mole ratio of said SiO2 to CaO is about 1:1.4.

5. The process as defined in claim 1, further comprising mixing said cesium and rubidium salt-containing solution with a saturated solution of an alkali salt or alkaline earth salt, said saturated solution containing anions which are the same as in said cesium and rubidium salt-containing solution.

* * * * *